United States Patent [19]
Jorgensen

[11] Patent Number: 4,602,632
[45] Date of Patent: Jul. 29, 1986

[54] BIO ABSORBABLE METAL HEMOSTATIC CLIP

[76] Inventor: Richard Jorgensen, 343 Maple, Lombard, Ill. 60148

[21] Appl. No.: 560,909

[22] Filed: Dec. 14, 1983

[51] Int. Cl.$^4$ ............................................. A61B 17/12
[52] U.S. Cl. .................................................... 128/325
[58] Field of Search ................ 128/325, 326, 337, 346

[56] References Cited

U.S. PATENT DOCUMENTS

| | | | |
|---|---|---|---|
| 3,006,344 | 10/1961 | Vogelfanger | 128/326 X |
| 3,363,628 | 1/1968 | Wood | 128/325 |
| 3,753,438 | 8/1973 | Wood et al. | 128/346 X |
| 4,269,190 | 5/1981 | Behney | 128/325 |

OTHER PUBLICATIONS

E. W. Andrews, Absorbable Metal Clips as Substitutes for Ligatures and Deep Sutures in Wound Closure, 1917.

M. G. Seelig, A Study of Magnesium Wire as an Absorbable Suture and Ligature Material, 1924.

P. N. Sawyer, Long Term Potency of Solid Wall Vascular Prostheses, 1965.

C. J. Schaefer, et al, Absorbable Ligating Clips, 1902.

*Primary Examiner*—Michael H. Thaler
*Attorney, Agent, or Firm*—James N. Videbeck

[57] ABSTRACT

An improved hemostatic clip for use in occluding blood vessels during surgical procedures is disclosed which is formed of bio-absorbable magnesium and is shaped to minimize any effects of the brittle properties of magnesium during use. The metallic bio-absorbable clip is smaller in size than existing non-metallic, bio-absorbable clips and eliminates the need for a locking mechanism structure on the clip.

1 Claim, 8 Drawing Figures

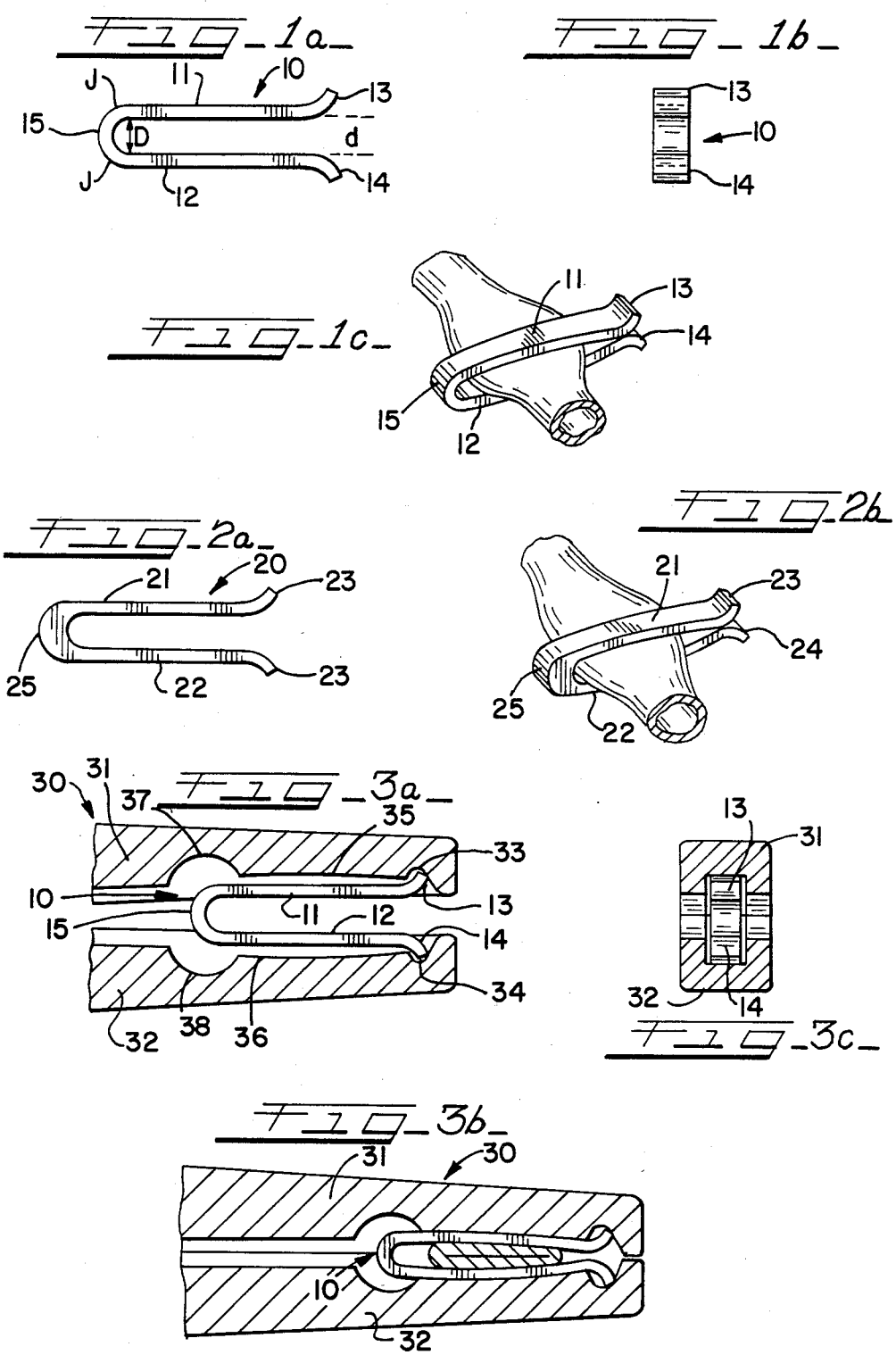

BIO ABSORBABLE METAL HEMOSTATIC CLIP

BACKGROUND OF THE DISCLOSURE

This invention relates generally to clips for use in closing blood vessels during surgical procedures. More particularly, this invention relates to a metallic, ligating clip which, in time, is absorbed by the body in which it is positioned, thereby avoiding the necessity of reopening a wound closure to remove the clip, and to an applicator for applying same.

In the early part of the twentieth century, the desirable bio-absorbable properties of magnesium were initially suggested as a potential beneficial material for use in sutures and ligatures, as discussed in Andrews, E. W.: Absorbable Metal Clips as Substitutes for Ligatures and Deep Sutures, J.A.M.A. 69:278 (July 28, 1917). However, a later study including in vivo and in vitro tests indicated that while magnesium wire was a desirable material because of its absorbability by the human body, its ultimate conclusion was that undesirable properties of gas formation during absorption, and hemolysis of blood cells found during prolonged contact with magnesium, in vitro, were potentially greater than the proposed benefits. M. G. Seelig, MD: A Study of Magnesium Wire as an Absorbable Suture and Ligature Material, Arch. Surg. 8:669-680, 1924. After this second article, discussion in the literature of the use of magnesium wire for suture or ligature material ceased, as far as is known. Additionally the Seelig article dealt solely with the use of an absorbable metal as a wire which could be knotted by a doctor applying the suture or ligature. The Seelig article does not address itself to ligature clips, which requires less metal deformation during application than does a suture.

While the use of metallic hemostatic clips has increased over the years, the development of stable, unchanging metal clips made of silver, and later tantalum, which would not degrade when position in the body has been of prime importance. However, the use of such clips during surgery, may require a later second operation in order to remove those clips from the patient's body after certain healing has taken place. Such a stable, non-absorbable hemostatic clip is shown in U.S. Pat. No. 3,363,628.

It is understood that heretofore known stable metallic ligature clips are considered by many doctors to be incompatible with the use of computer anatomical tomography (Cat Scan) equipment. Metal clips interfere with the passage of signals through the body in order to provide the computer generated pictures. Such pictures are especially important in viewing the healing process and the detection of diseases such as, cancer.

Partially in response to the above noted problem, a non-metallic absorbable ligating clip which degrades and is absorbed by the body after a predetermined period of time eliminating the possible need for a second operation to remove the clips was developed, as disclosed in Schaefer and Geelhoed, Surgery, Gynecology and Obstetrics, April, 1982, Volume 154, 513-516. The non-metallic clips disclosed are made of an extruded polymer flexible monofilament structure which may be clamped around a ligature. However, the elasticity of the material requires that a mechanical locking structure be designed into the clip, thus making the clip larger than previous metallic ligating clip, which would maintain its crimped or closed position once it was plastically deformed. As a result of the increased size of existing non-metallic absorbable ligating clips, blood vessels must be isolated from surrounding body tissues or organs to allow the clamp to be fastened onto the blood vessel and the locking mechanism closed thereon. There exists multiple instances where the use of the above, mentioned clips are impossible due to interference of the locking mechanism by surrounding tissues.

Meanwhile, research directed to other areas than sutures and ligature clips, disclosed that the use of a magnesium tube as a prostheses for replacing a part of an animal's aorta showed no toxicity in the system when implanted therein. Sawyer et al, Long-term Patency of Solidwall Vascular Prosthesis, Archives of Surgery, Volume 91, November, 1965, 735-742. Additional articles in the technical literature indicate that the use of magnesium in orthopedics, while yielding no adverse side effects, is not a desirable material for use as screws, rods, etc. in bone healing, as it is absorbed faster than the bone healing process takes place.

A need has developed for an improved absorbable ligature clip which maintains a closed position once placed over a blood vessel and closed thereon without the need for a locking mechanism on the ligature clip itself.

It is therefore, an object of the present invention, generally stated, to provide a new and improved absorbable metal ligature clip.

Another object of the present invention is the provision of an absorbable metallic ligating clip, including means for preventing destructive crimping thereof when position around a ligature.

SUMMARY OF THE INVENTION

The invention is directed to a hemostatic clip including a pair of arm members extending in close spatially oriented. Generally like direction from a central bight portion when in open position, the being of metal structure made of non-toxic bio-absorable material.

The invention is further directed a hemostatic clip as defined above wherein the bight portion has a larger mass than the arms thereof for increased strength and less deformation upon closing of the clip.

The invention is further directed to an applicator for a hemostatic clip which provides for closing a clip on a blood vessel without crimping the bight portion of the clip.

BRIEF DESCRIPTION OF THE DRAWINGS

The features of the present invention, which are believed to be novel, are set forth with particularity in the appended claims. This invention, together with further objects and advantages thereof, may best be understood by reference to the following description taken in connection with the accompanying drawings, in the several figures of which like reference numerals identify like elements, and in which:

FIG. 1a is a side elevational view of an absorbable metallic ligature clip constructed in accordance with the present invention in an open unused configuration.

FIG. 1b is an end elevational view of the ligature clip shown in figure in FIG. 1a.

FIG. 1c is a side elevational view of the ligature clip of FIG. 1a shown in its closed condition around a blood vessel, which is shown in section.

FIG. 2a is a side elevational view of a second embodiment of the ligature clip of the present invention shown in open configuration.

FIG. 2b is a side elevational view of the clip of FIG. 2a shown in closed configuration around a blood vessel, which is shown in section.

FIG. 3a is a side elevational view of a ligature clip constructed in accordance with the present invention as shown mounted in a clip applicator.

FIG. 3b is a side elevational view similar to FIG. 3a with the clip applicator squeezed to close the ligature clip of the present invention around a blood vessel.

DESCRIPTION OF THE PREFERRED EMBODIMENTS

As a result of the Seelig publication of in vitro tests showing hemolysis or break down of blood cells when positioned in prolonged contact with a strip of magnesium in a petri dish under laboratory conditions, the potential use of magnesium for hemostatic clips was effectively abandoned. However, later testing with a magnesium tube as a prothesis in an animal heart aorta, yielding no such detrimental test results, showed that contact of magnesium with blood cells produced no deleterious results. It is submitted that the use of a magnesium hemostatic clip on the outside of a blood vessel to clamp same closed does not produce any deleterious hemolysis to blood cells inside the closed blood vessel. Furthermore, the production of gases on the outside of a blood vessel as the magnesium clip oxidizes during absorption may be handled by the body without deleterious effect.

Heretofore, pure magnesium has been considered the best product for ligatures, as alloying magnesium has tended to produce a stronger but more brittle material. When using magnesium as a hemostatic clip, the brittle qualities of magnesium should be taken into consideration, both in the design of the clip and its application to a blood vessel.

Referring to FIG. 1a, a hemostatic clip 10, constructed in accordance with the present invention, includes a pair of substantially straight arm members 11, 12, each having an outwardly extending distal tab 13, 14, respectively, and each arm meeting at central bight portion 15. At the juncture between bight portion 15, and arms 11, 12, shown at J—J in dotted line, the distance D between the bases of arms 11, 12 is smaller than heretofore known in hemostatic clips. Likewise, the distance d between the inner portion of the distal ends 13, 14 of hemostatic clip 10 is smaller than such a measurement in heretofore known hemostatic clips when in the open position. Similarly to known hemostatic clips, the clips of the present invention come in varying sizes depending on the size of the blood vessels they are to close. However, smaller clips are utilized than heretofore known in order to reduce the deformation to closure of the clips. The outwardly flared tabs 13, 14 allow the clip 10 to be pushed onto a blood vessel during the application of the hemostatic clip. The small distances D and d relative to the length of arms 11, 12 provide for minimizing the deformation of arms 11, 12 during closure of the clip 10, as shown in FIG. 1c, and to avoid crimping the bight portion 15 so as to weaken the clip. With the tensile strength of magnesium, especially pure magnesium, being low, closure of the clip 10 by pushing together flared tips 13, 14 provides plastic deformation of arms 11, 12 along the length thereof without a strength destroying deformation of the bight portion 15. The embodiment shown in FIGS. 1a-c is especially adapted to be produced from extruded magnesium strip. It may be bent into position at an elevated temperature (however, not above the 800 degrees Fahrenheit flash point of magnesium) and anealed to reduce brittleness.

As shown in FIGS. 2a-b, the hemostatic clip 20 of the second embodiment is similar to clip 10 in that it has opposed elongate arm members 21, 22 each having flared distal ends 23, 24 and each being joined by a bight portion 25. However, in the second embodiment of the present invention the bight portion 25 is considerably thicker in axial cross section than at the arms 21, 22, thus strengthening the bight portion of the clip. As shown FIG. 2b, when the flared tips 23, 24 are pushed together thus bending arms 21, 22, there is very little movement along the lower ends of the arms or at the bight portion 25. This structure aids in preventing crimping of the bight portion and any attendant loss of strength.

Referring to FIGS. 3a and 3b, an actuating portion of a clip applicator is shown with the distal ends 31, 32, thereof, each including a recess 33, 34, for engaging the respective flared ends 13, 14, of the clip 10. Also each arm includes an axially oriented recess 31a, 32a which is rectangular in cross section and positioned along the inwardly racing surfaces of arm ends 31, 32. Each recess includes a slight concave curvature in the recess side wall at 35, 36, respectively, thus urging the distal end of the arms 11, 12, toward closure more than the portion of the arms toward the bight portion 15 of the clip. Inwardly adjacent to each concave side wall portion 35, 36, is a cutout portion 37, 38, respectively, which is positioned adjacent the bight portion 15 of a clip 10 when it is inserted in the applicator. As shown in FIG. 3b, when the applicator closes the clip the cut-out portions 37, 38, allow the clip to be closed without crimping the bight portion 15.

While two embodiments of the clip of the invention and one embodiment of an applicator therefor have been shown and described, it will be understood by those skilled in the art that modifications may be made within the scope of the invention without departing from the broader aspects thereof. Therefore, it is the aim of the appended claims to cover all such variations and modifications as call within the true spirit and scope of the invention.

The invention is claimed as follows:

1. A hemostatic clip for closing blood vessels, comprising:
    a body including a pair of elongate arm members extending in close spatially oriented, generally like direction from a central bight portion when in open position, said elongate arm members each having distal end portions and being plastically deformable adjacent said distal end portions for providing closure of said clip without substantial deformation of said bight portion thereof, said bight portion having a larger mass than said arms thereof for increased strength and less deformation upon closing, and said body being a metal structure made of nontoxic bio-absorbable material.

* * * * *